United States Patent [19]

Kirchhofer et al.

[11] Patent Number: 5,611,786
[45] Date of Patent: Mar. 18, 1997

[54] NEEDLE SYSTEM FASTENING MECHANISM

[75] Inventors: Fritz Kirchhofer, Sumiswald; Willy Michel, Burgdorf, both of Switzerland

[73] Assignee: Disetronic AG, Burgdorf, Switzerland

[21] Appl. No.: 387,870

[22] PCT Filed: Jul. 8, 1994

[86] PCT No.: PCT/CH94/00146

§ 371 Date: Feb. 27, 1995

§ 102(e) Date: Feb. 27, 1995

[87] PCT Pub. No.: WO95/01812

PCT Pub. Date: Jan. 19, 1995

[30] Foreign Application Priority Data

Jul. 9, 1993 [CH] Switzerland ............ 02067/93

[51] Int. Cl.⁶ .................... A61M 5/00; A61M 5/31
[52] U.S. Cl. ............. 604/240; 604/241; 604/232; 604/242
[58] Field of Search ............. 604/240, 232, 604/241–244, 201, 905, 227, 411, 415

[56] References Cited

U.S. PATENT DOCUMENTS

| | | | |
|---|---|---|---|
| 1,793,068 | 2/1931 | Dickinson | 604/242 |
| 2,828,743 | 4/1958 | Ashkenaz et al. | 604/193 |
| 2,834,346 | 5/1958 | Adams | 604/242 |
| 2,894,509 | 7/1959 | Bednarz | 604/202 |
| 3,278,357 | 10/1966 | Gettig et al. | 604/240 X |
| 4,340,148 | 7/1982 | Beckham | 604/241 X |
| 4,568,336 | 2/1986 | Cooper | 604/240 |
| 4,624,393 | 11/1986 | Lopez | 604/240 X |
| 5,205,833 | 4/1993 | Harsh et al. | 604/240 |

FOREIGN PATENT DOCUMENTS 737676   9/1955   United Kingdom .

*Primary Examiner*—Randall L. Green
*Assistant Examiner*—V. Alexander
*Attorney, Agent, or Firm*—Walter C. Farley

[57] ABSTRACT

A fastening mechanism for a needle system with the liquid system being a cartridge ampoule (4) and with a needle holder (3). The needle holder (3) is snapped onto the cartridge ampoule (4) or a cartridge ampoule holder containing the cartridge ampoule (4) by means of a snap-in closure means. The fastening mechanism of the invention allows sanitary application of injected medicines.

5 Claims, 2 Drawing Sheets

NEEDLE SYSTEM FASTENING MECHANISM

FIELD OF THE INVENTION

The present invention relates to a fastening mechanism for a needle system.

BACKGROUND OF THE INVENTION

Fastening mechanisms for needle systems are known for injection apparatus (hereafter frequently shortened to "apparatus"). The known injection apparatus is used to inject particular selectable quantities of liquids from a piston-fitted ampoule or cartridge-ampoule.

As regards cartridge-ampoules with a puncturable rubber membrane, the needles are screwed on in the manner of the state of the art. When the needle is screwed onto the cartridge-ampoule, the rear end of the needle pierces the membrane and as a result the advance of the stopper allows medicine to be expelled through the needle.

This procedure entails the drawback that rubber abrasion is caused by the rotational motion of the needle being screwed on. Frequently, abraded rubber particles will find their way into the medicine and may be introduced into the human body in the course of injection.

SUMMARY OF THE INVENTION

An object of the invention is to provide an improved fastening mechanism for an injection-apparatus needle system that provides a simple and sanitary, clean solution.

The above object is achieved by the invention by a snap closure means connecting the needle to the cartridge ampoule or the injection apparatus without rotation and in a simple manner.

Essentially, the advantages of the invention are that it makes possible sanitarily problem-free application of medicines by injection thanks to the fastening mechanism of the invention.

The fastening mechanism with the snap closure-means includes a fastening structure with snap-in teeth or detents on the needle holder and corresponding, matching elements on the cartridge ampoule or the holder containing the cartridge-ampoule.

BRIEF DESCRIPTION OF THE DRAWINGS

The Figures show an illustrative embodiment of the invention.

DESCRIPTION OF THE PREFERRED EMBODIMENTS

Figure 1:
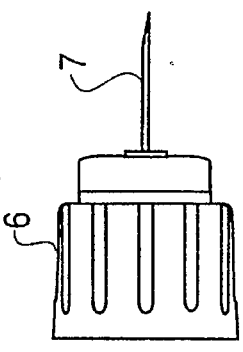
FIGS. 1 and 2 are side elevations, FIG. 1 in section, of a needle-holder of the state of the art.
Figure 2:
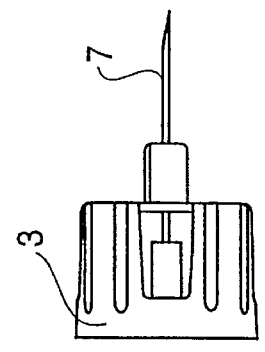

In the prior art, as shown in FIGS. 1 and 2, the needle holder is composed of a sleeve 6 fitted with an inside thread 10 or an outside thread, not shown, and a needle-seating support 11 for a needle 7. Both components are manufactured as one piece. The inside thread is screwed on the matching thread of the cartridge ampoule, as a result of which the needle pierces the rubber membrane and medicine can then be expelled through the needle. This kind of affixation inherently entails the drawback that the frequently abraded rubber particles find their way into the medicine.

Figure 3:
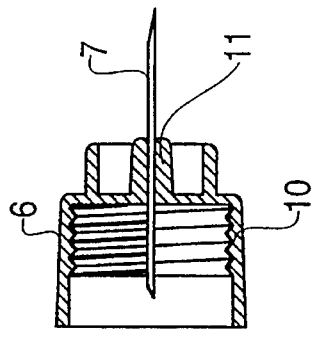
FIGS. 3 and 4 are similar views of the needle-holder of the invention.
Figure 4:
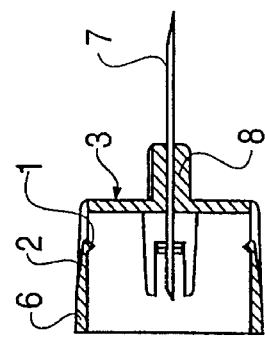
Figure 5:
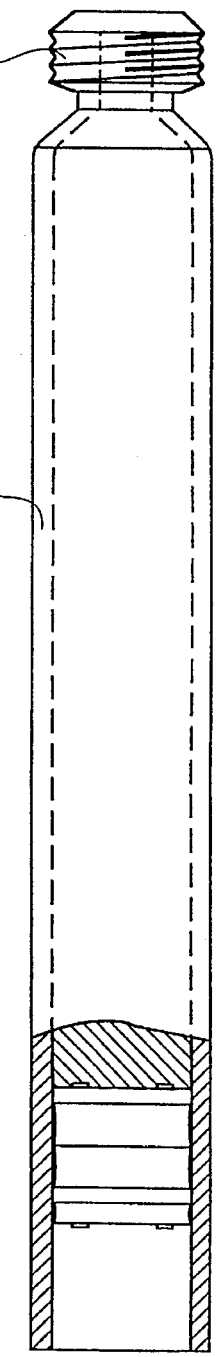
FIG. 5 is a side elevation of a cartridge ampoule.

The needle holder 3 in accordance with the invention shown in FIGS. 3 and 4 avoids this problem. Needle holder 3 has a sleeve 6 with a needle-seating support 8. The sleeve contains at least two pawls 2 with snap-in teeth 1. Together with the outside thread 5 of a cartridge ampoule 4, needle-holder 3 of the invention forms a snap-in closure means in that needle-holder 3 is slipped onto cartridge ampoule 4 and snap-in teeth 1 elastically enter threads 5 of cartridge ampoule 4.

Needle-holder 3 may be screwed off of threads 5 of cartridge ampoule 4 by rotation, or off a cartridge-ampoule holder containing said cartridge-ampoule, or it may be forcefully pulled off. Snap-in teeth 1 are arranged in such manner as to approximately match the pitch of the thread. Pawls 2 are recessed in such a way that in the event of disadvantageous positioning, that is when snap-in teeth 1 come to rest on the crest of the thread, pawl 2 does not see beyond the outer edge of needle-holder 3.

At least two or three or more pawls 2 are distributed at mutually equidistant angles around the circumference of needle holder 3.

Figure 6:
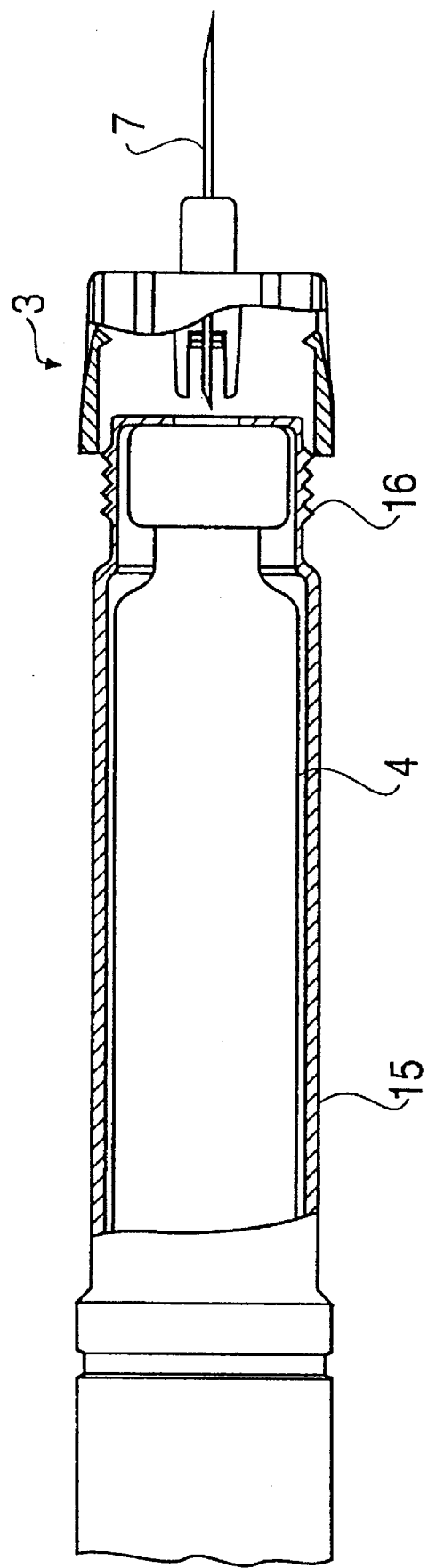
FIG. 6 is a side elevation, in partial section, of an ampoule holder with a needle-holder in accordance with the invention.

FIG. 6 shows an ampoule holder 15 having a threaded end 16, similar to threaded end 5, to receive a needle-holder in accordance with the invention, the ampoule holder being otherwise conventional.

We claim:

1. A fastening mechanism comprising the combination of a needle holder;

a generally cylindrical cartridge ampoule means containing a liquid;

means at an end of said cartridge ampoule means defining a helically extending radial protrusion; and a plurality of radially flexible pawl means on said needle holder for engaging said radial protrusion wherein said needle holder is repeatedly attachable to said cartridge ampoule means by a substantially linear motion in which said pawl means snap over said protrusion and being repeatedly detachable therefrom by rotational motion in which said pawl means follow said helical protrusion.

2. A fastening mechanism according to claim 1 wherein said cartridge ampoule means comprises an ampoule holder for receiving an ampoule, said helically extending radial protrusion on said cartridge ampoule means being formed on said ampoule holder.

3. A fastening mechanism according to claim 1 wherein said pawl means includes at least two pawls, each pawl having a snap-in tooth.

4. A fastening mechanism according to claim 3 wherein said helically extending protrusion is a thread, and wherein said teeth are positioned on said pawls to match the pitch of said thread.

5. A fastening mechanism according to claim 4 wherein said needle holder has an outer surface and wherein said pawls are recessed inwardly of said outer surface so that, when a tooth carried by one said pawl passes over a crest of said thread on said cartridge ampoule means, said pawl does not protrude outwardly beyond said outer surface.

* * * * *